US012667529B2

(12) United States Patent
Miller et al.

(10) Patent No.: US 12,667,529 B2
(45) Date of Patent: Jun. 30, 2026

(54) PRESERVATIVE SYSTEMS AND COMPOSITIONS COMPRISING THE SAME

(71) Applicant: Conopco, Inc., Englewood Cliffs, NJ (US)

(72) Inventors: Jamie Lynn Miller, North Haven, CT (US); Matthew Joseph Rienzo, Fairfield, CT (US)

(73) Assignee: Conopco, Inc., Hoboken, NJ (US)

( * ) Notice: Subject to any disclaimer, the term of this patent is extended or adjusted under 35 U.S.C. 154(b) by 418 days.

(21) Appl. No.: 18/021,063

(22) PCT Filed: Aug. 19, 2021

(86) PCT No.: PCT/EP2021/073005
§ 371 (c)(1),
(2) Date: Feb. 13, 2023

(87) PCT Pub. No.: WO2022/038218
PCT Pub. Date: Feb. 24, 2022

(65) Prior Publication Data
US 2023/0310292 A1 Oct. 5, 2023

(30) Foreign Application Priority Data
Aug. 21, 2020 (EP) ..................................... 20192090

(51) Int. Cl.
| | |
|---|---|
| *A61K 8/00* | (2006.01) |
| *A61K 8/368* | (2006.01) |
| *A61K 8/44* | (2006.01) |
| *A61K 8/46* | (2006.01) |
| *A61K 8/49* | (2006.01) |
| *A61Q 19/10* | (2006.01) |

(52) U.S. Cl.
CPC .............. *A61K 8/445* (2013.01); *A61K 8/368* (2013.01); *A61K 8/442* (2013.01); *A61K 8/466* (2013.01); *A61K 8/498* (2013.01); *A61Q 19/10* (2013.01); *A61K 2800/28* (2013.01); *A61K 2800/524* (2013.01); *A61K 2800/75* (2013.01)

(58) Field of Classification Search
None
See application file for complete search history.

(56) References Cited

U.S. PATENT DOCUMENTS

| | | | |
|---|---|---|---|
| 5,009,814 A | | 4/1991 | Kelkenberg et al. |
| 5,389,279 A | | 2/1995 | Au et al. |
| 5,393,466 A | | 2/1995 | Ilardi et al. |
| 7,582,681 B2 | | 9/2009 | Schmaus et al. |
| 9,661,847 B2 | | 5/2017 | Koshti et al. |
| 2012/0190744 A1 | | 7/2012 | Majeed et al. |
| 2016/0000669 A1 | | 1/2016 | Hinman et al. |
| 2016/0206537 A1 | | 7/2016 | Koshti et al. |
| 2018/0193243 A1 * | | 7/2018 | Koshti ..................... C11D 1/37 |
| 2020/0306172 A1 | | 10/2020 | Laboratoire |

FOREIGN PATENT DOCUMENTS

| | | | |
|---|---|---|---|
| WO | WO2004010958 | 2/2004 | |
| WO | WO2015136546 | 9/2015 | |
| WO | WVO2018142033 | 8/2018 | |
| WO | WO-2020069178 A1 * | 4/2020 | ............. A61K 8/345 |

OTHER PUBLICATIONS

Search Report and Written Opinion in EP20192090.pdf; Feb. 17, 2021.
Mintel; Fortifying Shampoo; Database GNPD Mintel [online]; Jun. 24, 2020; Online, the whole document, Database accession No. 7897871.
Mintel; Ultra Moisturising Mask; Database GNPD [Online] Mintel; Apr. 16, 2020; Online, the whole document, Database accession No. 7441615.
Mintel; 24HR Protection Deodorant Roll-On; Database GNPD [Online] Mintel; Feb. 3, 2020; Online, the whole document, database accession No. 7231775.
Search Report & Written Opinion in PCT/EP2021/073005; Dec. 9, 2021.
Kalia et al.; Nanofibrillated cellulose surface modification and potential applications; Colloid and Polymer Science; vol. 292, pp. 1-75; 2014.

* cited by examiner

*Primary Examiner* — Necholus Ogden, Jr.
(74) *Attorney, Agent, or Firm* — Edward A. Squillante, Jr.

(57) ABSTRACT

The invention is directed to a natural preservative system that comprises a substituted amino acid and with benzoic acid and/or a derivative thereof. The preservative system provides superior antimicrobial benefits and color stability to end use compositions even when the compositions are formulated to have a pH in the range of 3.5 to 8.2.

15 Claims, No Drawings

PRESERVATIVE SYSTEMS AND COMPOSITIONS COMPRISING THE SAME

FIELD OF THE INVENTION

The present invention is directed to a preservative system and compositions comprising the same. More particularly, the invention is directed to a preservative system that comprises a substituted amino acid in combination with benzoic acid and/or a derivative thereof. The preservative system of the present invention, surprisingly, provides superior antimicrobial benefits to end use compositions even when such compositions are formulated to have a pH in the range from 3.5 to 8.2.

Moreover, such a system unexpectedly provides superior antimicrobial benefits as well as excellent color stability when formulated in compositions substantially free of sodium dehydroacetate.

BACKGROUND OF THE INVENTION

DMDM hydantoin, parabens, methylisothiazolinone as well as methylchloroisothiazolinone are commonly used preservatives found in consumer products. Such preservatives have been safely used for years and are known to work well at maintaining the integrity and stability of certain end use compositions. Another preservative suitable for use in consumer products is sodium benzoate. However, sodium benzoate, while generally regarded as safe, is well known for use in compositions that are well within an acidic pH range. Notwithstanding, there is a desire to develop new preservative systems, and especially, systems that can include naturally derived components suitable to work well across a full range of consumer products formulated at a wide range of pH values. Preservative systems, including those that are naturally derived, should be effective at preserving products, not be skin sensitizing and not negatively impact the sensorial characteristics of consumer products, particularly those that are topically applied. They should also not induce any negative composition characteristics, like color change, to the products they are added to.

In addition to delivering superior antimicrobial benefits, the preservative systems should not be harmful to the environment and gentle enough for use on the most fragile consumer, babies.

This invention, therefore, is directed to a preservative system that can comprise naturally derived components and is suitable for use in compositions formulated at a wide range of pH values. The preservative system comprises a substituted amino acid with benzoic acid and/or a derivative thereof. The preservative system of the present invention, surprisingly, provides superior antimicrobial benefits to end use compositions even when such compositions are formulated to have a pH in the range from 3.5 to 8.2. Moreover, such a system unexpectedly does not negatively impact end use composition color and odor, and provides superior antimicrobial benefits when formulated in compositions substantially free of sodium dehydroacetate.

Additional Information

Efforts have been disclosed for making preservative systems. In U.S. Published Patent Application 2012/0190744A1, preservative systems for cosmetic formulations are described.

Still other efforts have been disclosed for making preservative systems. In U.S. Patent Application No. A1, non-toxic preservative compositions are described.

Even other efforts have been disclosed for making synergistic mixtures. In U.S. Pat. No. 7,582,681B2, antimicrobial active compounds with 1,2-alkane diols are described.

None of the additional information above describes a preservative system and end use composition with such a system as claimed in the present invention.

SUMMARY OF THE INVENTION

In a first aspect, the present invention is directed to a preservative system comprising:
  (a) a first component comprising a substituted amino acid; and
  (b) a second component comprising benzoic acid and/or a derivative thereof,
the first component and second component are present at a weight ratio from 1:4 to 4:1 wherein the composition optionally comprises sodium dehydroacetate, and when present, sodium dehydroacetate and the second component are present at amounts where the sodium dehydroacetate makes up less than 5% by weight (preferably, less than 3% and most preferably less than 2% by weight) of the total weight of sodium dehydroacetate and second component in the preservative system.

In a second aspect, the present invention is directed to a preservative system comprising:
  (a) a first component comprising a $C_6$ to $C_{20}$ aliphatic or alicyclic substituted amino acid; and
  (b) a second component comprising benzoic acid and/or a derivative thereof wherein the composition is substantially free of dehydroacetate.

In a third aspect, the present invention is directed to a preservative system comprising:
  (a) a first component comprising a substituted amino acid comprising decanoyl glycine, N-capryloyl glycine, N-undecylenoyl glycine, N-undecylenoyl phenylalanine or a mixture thereof;
  (b) a second component comprising sodium benzoate, potassium benzoate, amino benzoate or a mixture thereof, the first component and second component at a weight ratio of 1:4 to 4:1 wherein the composition is substantially free of sodium dehydroacetate.

In a fourth aspect, the present invention is directed to an end use composition comprising the preservative composition of the first, second and/or third aspect of the present invention, the end use composition being a product that is topically applied or orally ingested and having a pH in the range from 3.5 to 8.2.

In a fifth aspect, the present invention is directed to a method of preserving an end use composition, the method comprising the step of including in the end use composition the preservative composition of the first, second and/or third aspect of the present invention wherein the end use composition comprises from 30 to 82% by weight water.

In a sixth aspect, the present invention is directed to a method for treating skin by contacting the skin, cosmetically, with the end use composition of the fifth aspect of the invention.

In a seventh aspect, the present invention is directed to the use of the preservative system of the first or second aspect of the invention to preserve the color, aroma and microbiological stability of an end use composition.

All other aspects of the present invention will more readily become apparent from the description and examples which follow.

Skin, as used herein, is meant to include skin on the arms (including underarms), face, feet, neck, chest, hands, legs, buttocks and scalp (including hair). System, as used herein, means composition or formula, that includes a mixture of substituted amino acid and benzoic acid and/or a derivative thereof. Substituted amino acid includes a hydrocarbon/lipid substituted amino acid. End use composition is meant to include a composition ready for topical application such as a cream, lotion, balm, serum, gel, mousse, aerosol, deodorant, antiperspirant, shampoo, conditioner, make-up or personal wash, including bars and liquids. Such an end use composition may also be a food or beverage composition, a pharmaceutical composition (i.e., drug composition for medicinal purposes), oral supplement or a home care composition such as a hard surface cleaner or laundry detergent composition. In one embodiment, the end use composition is a liquid personal wash composition for non-therapeutic and cosmetic purposes (e.g., to remove dirt and/or odor causing bacteria), and most preferably, a non-therapeutic and cosmetic liquid body wash. In another embodiment, the end use composition is a shampoo composition. As hereinafter described, the end use composition of the present invention may optionally comprise skin benefit ingredients added thereto such as emollients, vitamins and/or derivatives thereof, resorcinols, retinoic acid precursors, colorants, moisturizers, sunscreens, mixtures thereof or the like. The skin benefit ingredients may be water or oil soluble. The end use composition, therefore, is an aqueous based composition with a pH from 3.5 to 8.2, and the composition can be water or oil continuous but is preferably water continuous. Viscosity, as used herein, is taken with a Brookfield helipath TD, at 4 rpm for 1 minute with temperature at 25° C. In still another embodiment, the end use composition of this invention is a non-therapeutic and cosmetic composition which is a leave-on skin lotion or cream. In the absence of explicitly stating otherwise, all ranges described herein are meant to include all ranges subsumed therein. As used herein, substantially free of means less than 0.0125% by weight. Color stability means no negative and discernible color change such as a white to brown color change. Antimicrobial benefits means at least a log kill of 2 at 14 days as described in General Chapter 51 of the United States Pharmacopeia (USP) whereby a log kill of under 2 at 14 days would be unacceptable, fail. The term comprising is meant to encompass the terms consisting essentially of and consisting of. For the avoidance of doubt, and for illustration, an end use composition of this invention comprising oil, water, sodium benzoate and substituted amine is meant to include a composition consisting essentially of the same and a composition consisting of the same. Except in the operating comparative examples, or where otherwise explicitly indicated, all numbers in this description indicating amounts or ratios of materials or conditions and/or physical properties of materials and/or use are to be understood as modified by the word "about".

DETAILED DESCRIPTION OF THE PREFERRED EMBODIMENTS

As to the preservative systems of the present invention, the first and second component are often at a weight ratio from 1:4 to 4:1, including all weight ratios subsumed therein. In an embodiment of the invention, the weight ratio of the first and second component is from 1:3 to 3:1 and in still another embodiment the weight ratio of the first to second component is 1:2 to 2:1, including all weight ratios subsumed therein.

Regarding the end use composition of the present invention, the total weight of first and second component is from 0.2 to 4% by weight of the total weight of the end use composition, including all ranges subsumed therein. In an embodiment of the invention, the total weight of first and second component is from 0.4 to 3% and in still another embodiment from 0.5 to 2% by weight of the total weight of the end use composition. In yet another embodiment, the total weight of first and second component in the end use composition is from 0.6 to 1.2% by weight of the total weight of the end use composition.

The first component comprises a substituted amino acid. Often, and preferably, the substituted amino acid comprises a $C_6$ to $C_{20}$, and preferably, a $C_7$ to $C_{18}$, and most preferably, a $C_3$ to $C_{12}$ aliphatic or alicyclic substituted amino acid. In an embodiment of the invention, the first component comprises from 1 to 3 of the substituted amino acids identified (i.e., decanoyl glycine, N-capryloyl glycine, N-undecylenoyl glycine and/or N-undecylenoyl phenylalanine). In another embodiment of the invention, the first component comprises from 1 to 2 of the substituted amino acids identified. In still another embodiment of the invention, N-capryloyl glycine or undecylenoyl glycine or both are present in the first component of the invention. In yet another embodiment of the invention, the first component is N-capryloyl glycine or undecylenoyl glycine, or a mixture thereof in a weight ratio of 1:5 to 5:1, and preferably, 3:1 to 1:3, and most preferably, 2:1 to 1:2 (even more preferably 1:1.5 to 1.5:1) including all weight ratios subsumed therein. In even another embodiment, the first component is undecylenoyl phenylalanine.

Regarding the second component, the same comprises benzoic acid and/or a derivative thereof. In an embodiment of the invention, the second component comprises a benzoic acid derivative like sodium benzoate, potassium benzoate, amino benzoate or a mixture thereof. In another embodiment of the invention, the second component comprises sodium benzoate or potassium benzoate, or both in a weight ratio of 1:5 to 5:1, and preferably, 3:1 to 1:3, and most preferably, 2:1 to 1:2 including all weight ratios subsumed therein. In still another embodiment, the second component is sodium benzoate or potassium benzoate or a mixture thereof. As to the amino benzoate, the preferred amino benzoate suitable for use includes sodium or potassium p-amino benzoate or a mixture thereof.

Sodium dehydroacetate is optional for use in the present invention, and when used typically makes up less than 0.0125% by weight of the end use composition with the preservative system of this invention. Therefore, the end use composition which employs the preservative composition of the present invention is substantially free of sodium dehydroacetate. In an embodiment of the invention, sodium dehydroacetate is present at 0.0001% to less than 0.075% by weight of the end use composition. In still another embodiment, the preservative system and end use composition are free of (i.e., 0.0% by weight) sodium dehydroacetate.

In yet another embodiment of the invention, the end use composition comprises from 30 to 82% by weight water, and preferably, from 40 to 80% by weight water, and most preferably, from 45 to 78% by weight water. In even another embodiment of the invention, the end use composition comprises from 50 to 77%, and preferably, from 52 to 76%, and most preferably, from 53 to 75% by weight water. In still another embodiment of the invention, the total weight of first component and total weight of second component in the preservative system are not equal and the total weight of first component in the preservative system is often 55 to 80%, and preferably, 58 to 75%, and most preferably, 60 to 70% of the weight of second component in the preservative system.

As to the end use compositions, the same can be beverages like tea beverages, sport-based beverages or the like. Tea beverages include those beverages prepared from tea plants such as the *Camellia sinensis* var. *sinensis* or *Camellia sinensis* var. *assamica* plants. They also include rooibos tea beverages obtained from the *Aspalathus linearis* plant. Tea beverage is intended to include beverages obtained from freshly picked tea leaves, and dried tea including those classified as black, oolong, green tea or mixtures thereof.

The sport-based beverages may be carbonated beverages (as long as the pH of the beverage is 3.5 or higher) and they can include vitamins, vegetable extracts, sweeteners, both artificial and natural, as well as caffeine.

The home care compositions may be hard surface cleaners, including table top, toilet and window cleaners as well as laundry detergents. Such compositions are conventional and aqueous based. Compositions which clean and disinfect surfaces often comprise solutions with surfactant to be poured, squirted or sprayed onto the surface targeted for cleaning. The solutions may be thickened with conventional thickeners to prevent them from draining off the surface too quickly. Particularly, for toilet cleaning purposes they are often packed in containers provided with a spout such that they may be delivered to the surface by squeezing the container. Such spouts are mounted on the container in such a way to allow for product evacuation in a consumer-friendly manner.

Laundry detergents suitable as end use compositions with the preservative system of the present invention can contain a surfactant system consisting of anionic surfactant, nonionic surfactant, or both, and optionally, a detergency builder, a soil release polymer (e.g., water-dispersible sulphonated polyester), fragrance and water.

In an embodiment of the invention, the end use composition is an emulsion and one which is topically applied to the body and left on the skin, scalp, nails and/or hair.

Oil employed in a topically applied end use composition (e.g., a leave-on composition) is limited only to the extent that same is a liquid at room temperature and suitable for use in a topical composition.

Illustrative examples of the oils suitable for use include silicone oils. Silicone oils may be divided into the volatile and non-volatile variety. The term "volatile" as used herein refers to those materials which have a measurable vapor pressure at ambient temperature. Volatile silicone oils are preferably chosen from cyclic or linear polydimethylsiloxanes containing from 3 to 9, and preferably, from 4 to 5 silicon atoms. Nonvolatile silicone oils useful in this invention include polyalkyl siloxanes, polyalkylaryl 5 siloxanes and polyether siloxane copolymers. Such essentially non-volatile polyalkyl siloxanes useful herein include, for example, polydimethylsiloxanes (like dimethicone) with viscosities of from 5 to 100,000 centistokes at 25° C. An often preferred silicone source is a cyclopentasiloxane and dimethicone solution.

Suitable esters for the end use composition with the preservative system of this invention include: (1) Alkenyl or alkyl esters of fatty acids having 10 to 20 carbon atoms like isopropyl palmitate, isopropyl isostearate, isononyl isonanonoate, oleyl myristate, isopropyl myristate, oleyl stearate, and oleyl oleate; (2) Ether-esters such as fatty acid esters of ethoxylated fatty alcohols; (3) Polyhydric alcohol esters such as ethylene glycol mono- and di-fatty acid esters, diethylene glycol mono- and di-fatty acid esters, polyethylene glycol (200-6000) mono and di-fatty acid esters, propylene glycol mono- and di-fatty acid esters, polypropylene glycol 2000 monooleate, polypropylene glycol 2000 mono stearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, poly-oxyethylene polyol fatty acid ester, sorbitan fatty acid esters, and polyoxy-ethylene sorbitan fatty acid esters; (4) Sterol esters, of which soya sterol and cholesterol fatty acid esters are examples thereof. Mixtures of the same are suitable for use as well.

Still other oils that may be used include triglycerides (animal and/or vegetable) like soybean oil (including hydrogenated soybean oil), sunflower oil, coconut oil, palm kernel oil, castor oil, rapeseed oil, palm oil, grape seed oil, shea butter, caprylic/capric triglyceride, safflower oil, fish oil or mixtures thereof.

Even other oils suitable for use include mineral oil, jojoba oil, isoparaffins, $C_{12}$-$C_{15}$ alkyl benzoates, polyalphaolefins, isohexadecane, petrolatum, mixtures thereof (including with those oils above) or the like. Soybean and sunflower oil are often preferred triglyceride oils. Caprylic/capric triglyceride is another often preferred oil to include in the end use compositions.

For oil continuous end use compositions, emulsifiers are suitable for use and they typically have an HLB from 2.5 to 7.5, and preferably, from 3 to 6.5, and most preferably, from 3 to 6, including all ranges subsumed therein. For water continuous end use compositions, the emulsifiers suitable for use typically have an HLB from over 7.5 to 18, and preferably, from 8 to 15, and most preferably, from 8 to 12, including all ranges subsumed therein. Such emulsifiers are preferred when the end use composition is, for example, a leave-on lotion or cream.

Illustrative examples of the types of emulsifiers that are suitable for use in such oil continuous emulsions are propylene glycol isostearate, glycol stearate sorbitan sesquioleate, lecithin, oleth-2, stearth-2, ceteth-2 glyceryl stearate, PEG-30 dipolyhydroxystearate. Still other emulsifiers suitable for use include glycol distearate, glyceryl oleate, sorbitan monooleate, sorbitan tristearate, sorbitan trioleate, sorbitan monopalmitate, lauryl PEG-10, (trimethylsiloxy) silylethyl dimethicone (Dow Corning® ES-5300) or mixtures thereof. For water continuous compositions, illustrative emulsifiers suitable for use include sorbitan laurate, polysorbate 20, polysorbate 85, oleth-10, ceteth 10, lecithin, peg-7 olivate, PEG-8 dioleate, Tween 40, 60, 80 or mixtures thereof.

Emulsifiers typically make up from 0.3 to 10, and preferably, from 2.5 to 8, and most preferably, from 3.5 to 7.5% by weight of the end use composition.

In an embodiment of the invention, the end use composition is a wash, including a liquid body wash, that is safe and gentle enough to use on babies. Such body washes will comprise conventional surfactant systems that may or may not include sulfates. The body washes can include, as surfactants, soaps and/or syndets.

As to anionic surfactants that may be used in the wash compositions, the same can include aliphatic sulfonates, such as a primary alkane (e.g., $C_8$-$C_{22}$) sulfonate, primary alkane (e.g., $C_8$-$C_{22}$) disulfonate, $C_8$-$C_{22}$ alkene sulfonate, $C_8$-$C_{22}$ hydroxyalkane sulfonate or alkyl glyceryl ether sulfonate (AGS); or aromatic sulfonates such as alkyl benzene sulfonate. The anionic may also be an alkyl sulfate (e.g., $C_{12}$-$C_{18}$ alkyl sulfate) or alkyl ether sulfate (including alkyl glyceryl ether sulfates). Among the alkyl ether sulfates are those having the formula:

$$RO(CH_2CH_2O)_nSO_3M$$

wherein R is an alkyl or alkenyl having 8 to 18 carbons, preferably 12 to 18 carbons, n has an average value of at least 1.0, and preferably, less than 5, and most preferably 1 to 4, and M is a solubilizing cation such as sodium, potassium, ammonium or substituted ammonium.

The anionic may also be alkyl sulfosuccinates (including mono- and dialkyl, e.g., $C_6$-$C_{22}$ sulfosuccinates); alkyl and acyl taurates (often methyl taurates), alkyl and acyl sarcosinates, sulfoacetates, $C_8$-$C_{22}$ alkyl phosphates and phosphonates, alkyl phosphate esters and alkoxyl alkyl phosphate esters, acyl lactates, $C_8$-$C_{22}$ monoalkyl succinates and maleates, sulphoacetates, alkyl glucosides and acyl isethionates, and the like.

Sulfosuccinates may be monoalkyl sulfosuccinates having the formula:

$$R^1O_2CCH_2CH(SO_3M)CO_2M;$$

and amide-MEA sulfosuccinates of the formula:

$$R^1CONHCH_2CH_2O_2CCH_2CH(SO_3M)CO_2M \text{ wherein} \\ R^1 \text{ ranges from } C_8\text{-}C_{22}\text{alkyl.}$$

Sarcosinates are generally indicated by the formula:

$$R^2CON(CH_3)CH_2CO_2M, \text{ wherein } R^2 \text{ ranges from} \\ C_8\text{-}C_{20}\text{alkyl.}$$

Taurates are generally identified by formula:

$$R^3CONR^4CH_2CH_2SO_3M$$

wherein $R^3$ is a $C_8$-$C_{20}$ alkyl, $R^4$ is a $C_1$-$C_4$ alkyl. M is a solubilizing cation as previously described.

End use wash compositions may contain $C_8$-$C_{18}$ acyl isethionates. These esters are prepared by a reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms.

The acyl isethionate may be an alkoxylated isethionate such as is described in Ilardi et al., U.S. Pat. No. 5,393,466, entitled "Fatty Acid Esters of Polyalkoxylated isethonic acid; issued Feb. 28, 1995; hereby incorporated by reference. This compound has the general formula:

$$R^5C\text{—}(O)\text{—}O\text{—}C(X)H\text{—}C(Y)H\text{—} \\ (OCH_2\text{—}CH_2)_m\text{—}SO_3M$$

wherein $R^5$ is an alkyl group having 8 to 18 carbons, m is an integer from 1 to 4, X and Y are each independently hydrogen or an alkyl group having 1 to 4 carbons and M is a solubilizing cation as previously described.

In an embodiment of the invention, the anionic surfactant used is sodium lauroyl glycinate, sodium cocoyl glycinate, sodium lauroyl glutamate, sodium cocoyl glutamate, sodium lauroyl isethionate, sodium cocoyl isethionate, sodium methyl lauroyl taurate, sodium methyl cocoyl taurate or a mixture thereof. Such anionic surfactants are commercially available from suppliers like Galaxy Surfactants, Clariant, Sino Lion and Innospec.

Amphoteric surfactants suitable for use in wash compositions (which depending on pH can be zwitterionic) include sodium acyl amphoacetates, sodium acyl amphopropionates, disodium acyl amphodiacetates and disodium acyl amphodipropionates where the acyl (i.e., alkanoyl group) can comprise a $C_7$-$C_{18}$ alkyl portion. Illustrative examples of the amphoteric surfactants suitable for use include sodium lauroamphoacetate, sodium cocoamphoacetate, sodium lauroamphoacetate, sodium cocoamphoacetate and mixtures thereof.

As to the zwitterionic surfactants which may be employed in wash compositions, such surfactants include at least one acid group. Such an acid group may be a carboxylic or a sulphonic acid group. They include often include quaternary nitrogen, and therefore, can be quaternary amino acids. They should generally include an alkyl or alkenyl group of 7 to 18 carbon atoms generally comply with an overall structural formula:

$$R^6\text{—}[\text{—}C(O)\text{—}NH(CH_2)_q\text{—}]_r\text{—}N^+\text{—}(R^7\text{—})(R^8)A\text{-}B$$

where $R^6$ is alkyl or alkenyl of 7 to 18 carbon atoms; $R^7$ and $R^8$ are each independently alkyl, hydroxyalkyl or carboxyalkyl of 1 to 3 carbon atoms; q is 2 to 4; r is 0 to 1; A is alkylene of 1 to 3 carbon atoms optionally substituted with hydroxyl, and B is —$CO_2$— or —$SO_3$—.

Suitable zwitterionic surfactants for use in the present invention and within the above general formula include simple betaines of formula:

$$R^6\text{—}N^+\text{—}(R^7)(R^8)CH_2CO_2^-$$

and amido betaines of formula:

$$R^6\text{—}CONH(CH_2)_t\text{—}N^+\text{—}(R^7)(R^8)CH_2CO_2 \text{ where } t \\ \text{is 2 or 3.}$$

In both formulae $R^6$, $R^7$ and $R^8$ are as defined previously. $R^6$ may, in particular, be a mixture of $C_{12}$ and Ca alkyl groups derived from coconut oil so that at least half, preferably at least three quarters of the groups $R^6$ have 10 to 14 carbon atoms. $R^7$ and $R^3$ are preferably methyl.

A further possibility is that the zwitterionic surfactant is a sulphobetaine of formula:

$$R^6\text{—}N^+\text{—}(R^7)(R^8)(CH_2)_3SO_3^-$$

or $$R^6\text{—}CONH(CH_2)_u\text{—}N^+\text{—}(R^7)(R^8)(CH_2)_3SO_3^-$$

where u is 2 or 3, or variants of these in which —$(CH_2)_3SO_3^-$ is replaced by —$CH_2C(OH)(H)CH_2SO_3^-$.

In these formulae, $R^6$, $R^7$ and $R^3$ are as previously defined.

Illustrative examples of the zwitterionic surfactants suitable for use include betaines like cocodimethyl carboxymethyl betaine, cocoamidopropyl betaine and laurylamidopropyl betaine. An additional zwitterionic surfactant suitable for use includes cocoamidopropyl sultaine. Such surfactants are made commercially available from suppliers like Stepan Company, and it is within the scope of the invention to employ mixtures of the aforementioned surfactants.

Nonionic surfactants may be used in the end use composition of the present invention. When used, nonionic surfactants are typically used at levels as low as 0.5, 1, 1.5 or 2% by weight and at levels as high as 6, 8, 10 or 12% by weight. The nonionics which may be used include in particular the reaction products of compounds having a hydrophobic group and a reactive hydrogen atom, for example aliphatic alcohols, acids, amides or alkylphenols with alkylene oxides, especially ethylene oxide either alone or with propylene oxide. Specific nonionic surfactant compounds are alkyl ($C_6$-$C_{22}$) phenols ethylene oxide condensates, the condensation products of aliphatic ($C_8$-$C_{18}$) primary or secondary linear or branched alcohols with ethylene oxide, and products made by condensation of ethylene oxide with the reaction products of propylene oxide and ethylenediamine. Other nonionic surfactants include long chain tertiary amine oxides, long chain tertiary phosphine oxides, dialkyl sulphoxides, and the like.

In an embodiment of the invention nonionic surfactants include fatty acid/alcohol ethoxylates having the following structures a) $HOCH_2(CH_2)_s(CH_2CH_2O)_v$ H or b) HOOC $(CH_2)_c(CH_2CH_2O)_d$ H; where s and v are each independently an integer up to 18; and c and d are each independently an integer from 1 or greater. In an embodiment of the invention, s and v are each independently 6 to 18; c and d are each independently 1 to 30. Other options for nonionic surfactants include those having the formula $HOOC(CH_2)_i$—CH=CH—$(CH_2)_k(CH_2CH_2O)_zH$, where i, k are each independently 5 to 15; and z is 5 to 50. In another embodiment of the invention, i and k are each independently 6 to 12; and z is 15 to 35.

The nonionic may also include a sugar amide, such as a polysaccharide amide. Specifically, the surfactant may be one of the lactobionamides described in U.S. Pat. No. 5,389,279 to Au et al., entitled "Compositions Comprising Nonionic Glycolipid Surfactants issued Feb. 14, 1995; which is hereby incorporated by reference or it may be one of the sugar amides described in U.S. Pat. No. 5,009,814 to Kelkenberg, titled "Use of N-Poly Hydroxyalkyl Fatty Acid Amides as Thickening Agents for Liquid Aqueous Surfactant Systems" issued Apr. 23, 1991; hereby incorporated into the subject application by reference.

In an embodiment of the invention, cationic surfactants may be used in the end use wash compositions.

One class of cationic surfactants includes heterocyclic ammonium salts such as cetyl or stearyl pyridinium chloride, alkyl amidoethyl pyrrylinodium methyl sulfate, and lapyrium chloride.

Tetra alkyl ammonium salts are another useful class of cationic surfactants suitable for use. Examples include cetyl or stearyl trimethyl ammonium chloride or bromide; hydrogenated palm or tallow trimethylammonium halides; behenyl trimethyl ammonium halides or methyl sulfates; decyl isononyl dimethyl ammonium halides; ditallow (or distearyl) dimethyl ammonium halides, and behenyl dimethyl ammonium chloride.

Still other types of cationic surfactants that may be used are the various ethoxylated quaternary amines and ester quats. Examples include PEG-5 stearyl ammonium lactate (e.g., Genamin KSL manufactured by Clariant), PEG-2 coco ammonium chloride, PEG-15 hydrogenated tallow ammonium chloride, PEG 15 stearyl ammonium chloride, dipalmitoyl ethyl methyl ammonium chloride, dipalmitoyl hydroxyethyl methyl sulfate, and strearyl amidopropyl dimethylamine lactate.

Still other useful cationic surfactants suitable for use include quaternized hydrolysates of silk, wheat, and keratin proteins, and it is within the scope of the invention to use mixtures of the aforementioned cationic surfactants.

If used, cationic surfactants will typically make up no more than 1.0% by weight of the end use composition. When present, they typically make up from 0.01 to 0.7%, and more typically, from 0.1 to 0.5% by weight of the end use wash composition, including all ranges subsumed therein.

In an embodiment of this invention, the end use wash composition can be substantially free of polymeric quaternary ammonium compounds (including salts of the same). In another embodiment, the wash will comprise less than 0.1% by weight polymeric quaternary ammonium compounds. In yet another embodiment, the wash will comprise less than 0.01% by weight polymeric quaternary ammonium compounds. In even another embodiment, the wash is free of polymeric quaternary ammonium compounds (i.e., 0.0%).

Water, in still another embodiment of the invention, makes up from 70 to 80% by weight of the end use composition, including all ranges subsumed therein.

In an embodiment of the invention, the pH of the end use composition (or preservative system when water is present) is from 4.5 to 8.0. In still another embodiment of the invention, the pH of the end use composition is from 5.2 to 7.8. In yet another embodiment of the invention, the pH of the composition is from over 6 to 7.7, and preferably, from 6.2 to 7.5, and most preferably, from 6.4 to 7.1, including all ranges subsumed therein. In another embodiment, the end use composition has a pH from 6.5 to 7.1, and in still another embodiment, from 6.6 to 7.1.

Adjusters suitable to modify the pH of the preservative systems and end use compositions of this invention may be used. Such pH adjusters include triethylamine, NaOH, KOH, $H_2SO4$, HCl, $C_6H_8O_7$ (i.e., citric acid) or mixtures thereof. The pH adjusters are added at amounts such that the final pH of the preservative system (when water is included) and end use composition are each, independently, from 3.5 to 8.2, including all ranges subsumed therein.

The pH of the water phase is assessed by using conventional instrumentation such as a pH meter made commercially available from Thermo Scientific®.

As to the optional skin benefit agents suitable for use in this invention, the same are limited only to the extent that they are capable of being topically applied, and compatible in the end use composition at the desired pH.

Illustrative examples of the benefit agents suitable to include in the water portion of such compositions are acids, like amino acids, such as arginine, valine or histidine. Additional water-soluble benefit agents suitable for use include vitamin $B_2$, niacinamide (vitamin $B_3$), vitamin $B_6$, vitamin C, mixtures thereof or the like. Water soluble derivatives of such vitamins may also be employed. For instance, vitamin C derivatives such as ascorbyl tetraisopalmitate, magnesium ascorbyl phosphate and ascorbyl glycoside may be used alone or in combination with each other. Other water-soluble benefit agents suitable for use include 4-ethyl resorcinol, extracts like sage, aloe vera, green tea, grapeseed, thyme, chamomile, yarrow, cucumber, liquorice, rosemary extract or mixtures thereof. Water soluble sunscreens like ensulizole may also be used. Total amount of optional water-soluble benefit agents (including mixtures) when present in the end use composition of the invention may range from 0.0 to 10%, preferably from 0.001 to 8%, and most preferably, from 0.01 to 6% by weight, based on total weight of the end use composition and including all ranges subsumed therein.

It is also within the scope of the present invention to optionally include oil (i.e., non-water) soluble benefit agents. The only limitation with respect to such oil soluble benefit agents are that the same are suitable to provide a benefit to skin when topically applied.

Illustrative examples of the types of oil soluble benefit agents that may optionally be used in the end use composition of this invention include components like stearic acid, vitamins like vitamin A, D, E and K (and their oil soluble derivatives), sunscreens like ethylhexylmethoxycinnamate, bis-ethyl hexyloxyphenol methoxyphenol triazine, 2-ethylhexyl-2-cyano-3,3-diphenyl-2-propanoic acid, drometrizole trisiloxane, 3,3,5-trimethyl cyclohexyl 2-hydroxybenzoate, 2-ethylhexyl-2-hydroxybenzoate or mixtures thereof.

Other optional oil soluble benefit agents suitable for use include resorcinols like 4-hexyl resorcinol, 4-phenylethyl resorcinol, 4-cyclopentyl resorcinol, 4-cyclohexyl resorcinol 4-isopropyl resorcinol or a mixture thereof. Also, 5-substituted resorcinols like 4-cyclohexyl-5-methylbenzene-1,3-diol, 4-isopropyl-5-methylbenzene-1,3-diol, mixtures thereof or the like may be used. The 5-substituted resorcinols, and their synthesis are described in commonly assigned U.S. Published Patent Application No. 2016/0000669A1.

Even other oil soluble actives suitable for use include omega-3 fatty acids, omega-6 fatty acids, climbazole, farnesol, ursolic acid, myristic acid, geranyl geraniol, oleyl betaine, cocoyl hydroxyethyl imidazoline, hexanoyl sphingosine, 12-hydroxystearic acid, petroselinic acid, conjugated linoleic acid, stearic acid, palmitic acid, lauric acid, terpineol, thymol mixtures thereof or the like.

In an embodiment of the invention, the optional oil soluble benefit agent used is a retinoic acid precursor. Preferably, the retinoic acid precursor is retinol, retinal, retinyl propionate, retinyl palmitate, retinyl acetate or a mixture thereof. Retinyl propionate, retinyl palmitate and mixtures thereof are typically most preferred.

When optional (i.e., 0.0 to 1.5% by weight) oil soluble active is used in the oil phase of the end composition of the invention, it typically makes up from 0.001 to 1.3%, and in another embodiment, from 0.05 to 1.2%, and in yet another embodiment, from 0.1 to 0.5% by weight of the total weight of the end use composition.

If desired, traditional preservatives may optionally be included (in addition to the preservative system of this invention) in the end use compositions to protect against the growth of potentially harmful microorganisms. Cosmetic chemists are familiar with appropriate preservatives and routinely choose them to satisfy the preservative challenge test and to provide product stability. Suitable traditional but optional preservatives for use include hydantoin derivatives and propionate salts. Particularly preferred preservatives are iodopropynyl butyl carbamate, phenoxyethanol, hydroxyacetophenone, ethylhexylglycerine, methyl paraben, propyl paraben, imidazolidinyl urea, dimethyl-dimethyl (DMDM) hydantoin and benzyl alcohol and mixtures thereof. Another preservative suitable for use includes chlorophenesin. The preservatives should be selected having regard for the use of the composition and possible incompatibilities between the preservatives and other ingredients in the emulsion. These optional preservatives, when used, may be employed in amounts ranging from 0.001% to 2% by weight of the total weight of the end composition, including all ranges subsumed therein. In a preferred embodiment of the invention, only the preservative system of the present invention is used without any additional and optional preservatives.

It is also within the scope of the present invention to use conventional preservative enhancers like hexylene glycol and 1,2-octane diol and the like, typically from 0.2 to 1% by weight of the end use composition.

In an option but preferred embodiment of the invention, the benzoic acid used in the invention is natural, and therefore, obtained from sources like fruits, vegetables, berries and seafood and the derivatives of the same, like sodium benzoate, are derived from benzoic acid found naturally. The benzoic acid derivatives, therefore, are prepared by standard neutralization reactions of benzoic acid.

Thickening agents are optionally suitable for use in the end use composition of the present invention. Particularly useful are the polysaccharides. Examples include fibers, starches, natural/synthetic gums and cellulosics. Representative of the starches are chemically modified starches such as sodium hydroxypropyl starch phosphate and aluminum starch octenylsuccinate. Tapioca starch is often preferred, as is maltodextrin. Suitable gums include xanthan, *sclerotium*, pectin, karaya, arabic, agar, guar (including Acacia senegal guar), carrageenan, alginate and combinations thereof. Suitable cellulosics include hydroxypropyl cellulose, hydroxypropyl methylcellulose, ethylcellulose, sodium carboxy methylcellulose (cellulose gum/carboxymethyl cellulose) and cellulose (e.g. cellulose microfibrils, cellulose nanocrystals or microcrystalline cellulose). Sources of cellulose microfibrils include secondary cell wall materials (e.g. wood pulp, cotton), bacterial cellulose, and primary cell wall materials.

Preferably the source of primary cell wall material is selected from parenchymal tissue from fruits, roots, bulbs, tubers, seeds, leaves and combination thereof; more preferably is selected from citrus fruit, tomato fruit, peach fruit, pumpkin fruit, kiwi fruit, apple fruit, mango fruit, sugar beet, beet root, turnip, parsnip, maize, oat, wheat, peas and combinations thereof; and even more preferably is selected from citrus fruit, tomato fruit and combinations thereof. A most preferred source of primary cell wall material is parenchymal tissue from citrus fruit. Citrus fibers, such as those made available by Herbacel® as AQ Plus can also be used as source for cellulose microfibrils. The cellulose sources can be surface modified by any of the known methods including those described in Colloidal Polymer Science, Kalia et al., "Nanofibrillated cellulose: surface modification and potential applications" (2014), Vol 292, Pages 5-31.

Synthetic polymers are yet another class of effective thickening agent. This category includes crosslinked polyacrylates such as the Carbomers, acrylate copolymers, acrylates/acrylate ($C_{10}$-$C_{30}$) alkyl acrylate crosspolymers, polyacrylamides such as Sepigel® 305 and taurate copolymers such as Simulgel® EG and Aristoflex® AVC, the copolymers being identified by respective INCI nomenclature as Sodium Acrylate/Sodium Acryloyldimethyl Taurate and Acryloyl DimethyltaurateNinyl Pyrrolidone Copolymer. Another preferred synthetic polymer suitable for thickening is an acrylate-based polymer made commercially available by Seppic and sold under the name Simulgel INS100. Calcium carbonate, fumed silica, and magnesium-aluminum-silicate may also be used.

The amounts of the thickening agent, when used, may range from 0.001 to 5%, by weight of the end use composition. Maltodextrin, xanthan gum, and carboxymethyl cellulose are the often preferred thickening agents.

The viscosity of the end use compositions is typically from 750 to 55,000 cps, and preferably, from 1,000 to 40,000 cps, and most preferably, from 2,500 to 30,000 cps.

Fragrances, fixatives, chelators (like EDTA) salts (like NaCl), opacifiers (like $TiO_2$) and exfoliants may optionally be included in the end use composition of the present invention. Each of these substances may range from about 0.03 to about 5%, preferably between 0.1 and 3% by weight of the total weight of the end use composition, including all ranges subsumed therein. To the extent the exfoliants are used, those selected should be of small enough particle size so that they do not impede the performance of any pump and actuator used to dispense the end use composition of this invention.

Conventional humectants may optionally be employed as additives in the present invention to assist in moisturizing skin when such emulsions are topically applied. These are generally polyhydric alcohol type materials. Typical polyhydric alcohols include glycerol (i.e., glycerine or glycerin), propylene glycol, dipropylene glycol, polypropylene glycol (e.g., PPG-9), polyethylene glycol, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof. Most preferred is glycerin, propylene glycol or a mixture thereof. The amount of humectant employed may range anywhere from 0.0 to 35% by weight of the total weight of the liquid and composition. Often, humectant makes up from 0.0 to 20%, and preferably, from 0.001 to 15% by weight (most preferably, from 2 to 12% by weight) of the total weight of the end use composition.

Another optional additive suitable for use includes hemp oil with 2.5 to 25% by weight cannabigerol and/or cannabidiol at from 0.5 to 10 percent by weight. When used, such oil makes up from 0.0001 to 12% by weight of the end use composition, and preferably, from 0.01 to 5% by weight of the end use composition, including all ranges subsumed therein.

When making the preservative system and end use composition of the present invention, the desired ingredients may be mixed using conventional apparatus under moderate shear and atmospheric conditions, with temperature being from ambient to 90° C.

The packaging for the end use composition is limited only to the extent that it is desired for use by consumers and suitable to carry the end use composition of the invention.

Typically, the packaging can be a bottle, jar, spray pump, tube or tub. Preferably, the packaging is durable yet light weight and comprises at least 10% by weight or more of post-consumer resin (PCR) to ensure that its impact on the environment is limited. In a preferred embodiment, the preservative system of the invention is natural or naturally derived and the packaging is all PCR or biodegradable.

The Examples provided are to facilitate an understanding of the invention. They are not intended to limit the scope of the claims.

EXAMPLES

The formulae in the Examples were made by mixing ingredients with moderate shear, under atmospheric conditions and at temperatures from about 35 to 70° C. Each formula made was split and weighed into 5 different/distinct aliquots. The 5 different aliquots were then inoculated with a respective organism or organism mix as identified below, resulting in challenged formulations. The inoculum was equal to 1% of the formula weight and at initiation did not alter the character of the formula being challenged. All formulae were thoroughly mixed manually after inoculation to distribute the respective microorganisms uniformly. The challenged formulations were then stored at about 25° C. for the duration of the test.

Challenged formulations were then sampled for viable microorganisms at 7 days, 14 days, and 28 days. These samples were plated in a petri dish and incubated under conventional conditions appropriate for such test organisms and as identified in the American Type Culture Collection (ATCC), with the middle point of ranges selected when criteria was defined by a range. After incubation, the number of microbial colonies was counted, and the resulting figure was multiplied by the appropriate dilution factor to obtain the number of microorganisms per sample unit.

| Final Formula A Chassis Body Wash | Weight % as Active |
|---|---|
| Ingredient | |
| Water | QS |
| Hydroxypropyl Starch Phosphate | 4.5 |
| Sodium Lauroyl Glycinate | 3.1 |
| Sodium lauroyl Isethionate | 3.1 |
| Lauric Acid | 2.8 |
| Fully Hydrogenated Soybean Oil | 2.4 |
| Soybean Oil | 1.6 |
| Stearic Acid | 0.3 |
| Glycerin | 0.9 |
| Guar Hydroxypropyltrimonium chloride | 0.3 |
| Cocamidopropyl betaine | 6.1 |
| NaCl | 0.3 |
| Preservative System (varies per batch) | Al |
| EDTA | 0.1 |
| Citric Acid | 0.2 |
| NaOH | 0.2 |
| Fragrance | 1.0 |
| Total | 100.00 |

Al—as later identified

| Final Formula O Chassis Body Wash | Weight % as Active |
|---|---|
| Ingredient | |
| Water | QS |
| PEG 150 Distearate | 0.1 |
| Sodium lauroyl Isethionate | 3.0 |
| Stearic Acid | 0.1 |
| Glycerin | 6.0 |
| Cocamidopropyl betaine | 6.0 |
| NaCl | 0.3 |
| Preservative System (varies per batch) | Al |
| EDTA | 0.1 |
| NaOH | 0.03 |
| Fragrance | 0.2 |
| Total | 100.00 |

Al—as later identified in the below Chassis

Antimicrobial Key

Pool 1: *Pseudomonas aeruginosa+Burkholderia cepacia* (gram negative)

Pool 2: *Klebsiella pneumoniae+Enterobacter gergoviae* (gram negative)

3: *Staphylococcus aureus* (Staph. aur.)

4: *Candida albicans* (Yeast)

5: *Aspergillus brasiliensis* (Mold)

Complete Eradication ("CE")—Destruction/Kill of all Antimicrobial Present

| Color Key | | |
|---|---|---|
| | (Observed by visual evaluation from about 10 trained panelists) | Pass/ Fail |
| 0 | White | Pass |
| 1 | Off White | Pass |
| 2 | Beige | Pass |
| 3 | Tan | Fail |
| 4 | Brown | Fail |

Color appearance was visually assessed at the times identified below.

Formula A Chassis with 0.5% Sodium Benzoate; 0.3% Capryloyl Glycine, pH 6.60

|  | 7 Day | 14 Day | 28 Day |
|---|---|---|---|
| Pool 1 | CE | CE | CE |
| Pool 2 | CE | CE | CE |
| *Staph. Aur.* | CE | CE | CE |
| Yeast | CE | CE | CE |
| Mold | 2.84 Log Reduction | 2.60 Log Reduction | CE |

Appearance/Color

| Temperature (° C.) | Initial | 2 weeks | 4 weeks | 12 weeks |
|---|---|---|---|---|
| 4 | 0 | — | — | — |
| 25 | — | 0 | 0 | 0 |
| 37 | — | 0 | 0 | 0 |
| 45 | — | 0 | 0 | 0 |

Formula A Chassis with 0.5% Sodium Benzoate; 0.3% Undecylenoyl Glycine, pH 6.66

|  | 7 Day | 14 Day | 28 Day |
|---|---|---|---|
| Pool 1 | CE | CE | CE |
| Pool 2 | CE | CE | CE |
| *Staph. Aur.* | CE | CE | CE |
| Yeast | CE | CE | CE |
| Mold | 2.53 Log Reduction | CE | CE |

Appearance/Color

| Temperature (° C.) | Initial | 2 weeks | 4 weeks | 8 weeks | 12 weeks |
|---|---|---|---|---|---|
| 4 | 0 | — | — | — | — |
| 25 | 0 | 0 | 0 | 0 | 0 |
| 37 | 0 | 0 | 0 | 0 | 0 |
| 45 | 0 | 0 | 0 | 0 | 0 |

Formula A Chassis with 0.5% Sodium Benzoate; 0.1% undecylenoyl glycine; 0.2% capryloyl glycine, pH 6.59

|  | 7 Day | 14 Day | 28 Day |
|---|---|---|---|
| Pool 1 | CE | CE | CE |
| Pool 2 | CE | CE | CE |
| *Staph. Aur.* | CE | CE | CE |
| Yeast | CE | CE | CE |
| Mold | 2.06 Log Reduction | 2.15 Log Reduction | 2.32 Log Reduction |

Appearance/Color

| Temperature (° C.) | Initial | 8 weeks |
|---|---|---|
| 4 | 0 | — |
| 25 | — | 2 |
| 37 | — | 2 |
| 45 | — | 2 |

Formula A Chassis with 0.5% Sodium Benzoate; 0.2% undecylenoyl glycine; 0.1% capryloyl glycine, pH 6.60

|  | 7 Day | 14 Day | 28 Day |
|---|---|---|---|
| Pool 1 | CE | CE | CE |
| Pool 2 | CE | CE | CE |
| *Staph. Aur.* | CE | CE | CE |
| Yeast | CE | CE | CE |
| Mold | 1.88 Log Reduction | 1.69 Log Reduction | 2.55 Log Reduction |

Appearance/Color

| Temperature (° C.) | Initial | 12 weeks |
|---|---|---|
| 4 | 0 | — |
| 25 | — | 2 |
| 37 | — | 2 |
| 45 | — | 2 |

Formula A Chassis with 0.5% Sodium Benzoate, pH 6.71

|  | 7 Day | 14 Day | 28 Day |
|---|---|---|---|
| Pool 1 | CE | CE | CE |
| Pool 2 | CE | CE | CE |
| *Staph. Aur.* | CE | CE | CE |
| Yeast | CE | CE | CE |
| Mold | 3.00 Log Reduction | 3.45 Log Reduction | 3.80 Log Reduction |

Appearance/Color

| Temperature (° C.) | Initial | 8 weeks | 12 weeks |
|---|---|---|---|
| 4 | 0 | — | — |
| 25 | — | 0 | 1 |
| 37 | — | 0 | 1 |
| 45 | — | 0 | 1 |

Formula A Chassis with 0.5% Sodium Benzoate; 0.3% Undecylenoyl phenylalanine, pH 6.64

|  | 7 Day | 14 Day | 28 Day |
|---|---|---|---|
| Pool 1 | CE | CE | CE |
| Pool 2 | CE | CE | CE |

17

-continued

Formula A Chassis with 0.5% Sodium Benzoate; 0.3% Undecylenoyl phenylalanine, pH 6.64

|  | 7 Day | 14 Day | 28 Day |
|---|---|---|---|
| *Staph. Aur.* | CE | CE | CE |
| Yeast | CE | CE | CE |
| Mold | 4.44 Log Reduction | 4.13 Log Reduction | CE |

Appearance/Color

| Temperature (° C.) | Initial | 8 weeks | 12 weeks |
|---|---|---|---|
| 4 | 0 | — | — |
| 25 | — | 0 | 1 |
| 37 | — | 0 | 1 |
| 45 | — | 0 | 1 |

Formula A with 0.5% Sodium Benzoate 0.15% undecylenoyl glycine; 0.15% capryloyl glycine; 0.1% dehydroacetate, pH 6.62

|  | 7 Day | 14 Day | 28 Day |
|---|---|---|---|
| Pool 1 | CE | CE | CE |
| Pool 2 | CE | CE | CE |
| *Staph. Aur.* | CE | CE | CE |
| Yeast | CE | CE | CE |
| Mold | CE | CE | CE |

Appearance/Color

| Temperature (° C.) | Initial | 2 weeks | 4 weeks | 8 weeks | 12 weeks |
|---|---|---|---|---|---|
| 4 | 0 | — | — | — | — |
| 25 | 0 | 1 | 2 | 2 | 3 |
| 37 | 0 | 1 | 2 | 3 | 4 |
| 45 | 0 | 1 | 3 | 3 | 4 |

Formula A with 0.5% Sodium Benzoate; 0.15% Undecylenoyl glycine; 0.15% capryloyl glycine; 0.01% dehydroacetate, pH 6.62

|  | 7 Day | 14 Day | 28 Day |
|---|---|---|---|
| Pool 1 | CE | CE | CE |
| Pool 2 | CE | CE | CE |
| *Staph. Aur.* | CE | CE | CE |
| Yeast | CE | CE | CE |
| Mold | 3.26 Log Reduction | 3.32 Log Reduction | 4.13 Log Reduction |

18

Formula A with 0.5% Sodium Benzoate; 0.15% Undecylenoyl glycine; 0.15% CG; 0.05% dehydroacetate, pH 6.59

|  | 7 Day | 14 Day | 28 Day |
|---|---|---|---|
| Pool 1 | CE | CE | CE |
| Pool 2 | CE | CE | CE |
| *Staph. Aur.* | CE | CE | CE |
| Yeast | CE | CE | CE |
| Mold | CE | CE | CE |

Appearance/Color

| Temperature (° C.) | Initial | 2 weeks | 4 weeks | 8 weeks | 12 weeks |
|---|---|---|---|---|---|
| 4 | 0 | — | — | — | — |
| 25 | 0 | 0 | 1 | 2 | 3 |
| 37 | 0 | 1 | 2 | 3 | 4 |
| 45 | 0 | 1 | 2 | 3 | 4 |

Formula A with 1:1:1:1 (0.2% sodium benzoate; 0.2% undecylenoyl glycine; capryloyl glycine; dehydroacetate, pH 6.69

|  | 7 Day | 14 Day | 28 Day |
|---|---|---|---|
| Pool 1 | CE | CE | CE |
| Pool 2 | CE | CE | CE |
| *Staph. Aur.* | CE | CE | CE |
| Yeast | CE | CE | CE |
| Mold | CE | CE | CE |

Appearance/Color

| Temperature (° C.) | Initial | 2 weeks | 4 weeks | 8 weeks | 12 weeks |
|---|---|---|---|---|---|
| 4 | 0 | — | — | — | — |
| 25 | 0 | 0 | 0 | 1 | 2 |
| 37 | 0 | 0 | 0 | 2 | 3 |
| 45 | 0 | 0 | 1 | 2 | 3 |

Formula O with; 0.6% Sodium Benzoate; 0.15% undecylenoyl glycine; 0.15% capryloyl glycine, pH 6.56

|  | 7 Day | 14 Day | 28 Day |
|---|---|---|---|
| Pool 1 | CE | CE | CE |
| Pool 2 | CE | CE | CE |
| *Staph. Aur.* | CE | CE | CE |
| Yeast | CE | CE | CE |
| Mold | 1.94 Log Reduction | 2.36 Log Reduction | 1.86 Log Reduction |

The data recovered demonstrates that when preservative systems are prepared and used according to the present invention, excellent antimicrobial benefits (a log kill of at least 2, complete eradication) are achieved along with color stability, and surprisingly, when formulating compositions with no dehydroacetate. Moreover, the trained panelists also concluded that the preservative systems used according to this invention did not adversely impact the aroma of the compositions they were formulated in and the compositions did not, in situ, yield any malodors after the stability tests were complete.

Compositions made inconsistent with the invention, i.e., the composition with Formula O as the chassis, did not demonstrate superior antimicrobial benefits.

The invention claimed is:

1. A wash composition comprising a preservative system, an acyl isethionate, a zwitterionic surfactant comprising a betaine, a sultaine or both and the composition has a pH from 6 to 7.8, wherein the preservative system comprises:

(a) a first component comprising a substituted amino acid; and (b) a second component comprising benzoic acid and/or a derivative thereof, wherein the first component and second component are present at a weight ratio from 1:4 to 4:1, and further wherein the composition optionally comprises sodium dehydroacetate, and when present, the sodium dehydroacetate and the second component are present at amounts where the sodium dehydroacetate makes up less than 5% by weight based on total weight of sodium dehydroacetate and second component in the preservative system, the composition comprising from 30 to 82% by weight water and wherein no preservative is present in the composition in addition to the first component and second component, and further wherein the first component is decanoyl glycine, N-capryloyl glycine, N-undecylenoyl glycine, N-undecylenoyl phenylalanine or a mixture thereof; and the second component is sodium benzoate, potassium benzoate, amino benzoate or a mixture thereof, and the zwitterionic surfactant is a betain comprising cocamidopropyl betaine, and the acyl isethionate, is sodium lauroyl isethionate, sodium cocyl isethionate or a mixture thereof, and the composition comprises an additional surfactact comprising sodium lauroyl glycinate, sodium cocoyl glycinate, sodium methyl lauroyl taurate, sodium methyl cocoyl taurate or a mixture thereof.

2. The composition according to claim 1, wherein the composition comprises less than 0.125% by weight sodium dehydroacetate and the composition comprises from 40 to 80% by weight water.

3. The composition according to claim 2, wherein the composition has a pH from 6 to 7.5 and comprises sodium lauroyl isethionate and the additional surfactant is sodium lauroyl glycinate.

4. The composition according to claim 2, wherein the first component is N-capryloyl glycine or undecylenoyl glycine or a mixture thereof, the second component is sodium benzoate, and the composition comprises additional surfactant which is sodium methyl lauroyl taurate, cocamidopropyl betaine and sodium lauroyl isethionate.

5. The composition according to claim 1, wherein the composition is a baby wash.

6. The composition according to claim 2, wherein the first and second components are present in the composition at a total weight of 0.2 to 4% by weight of the composition, the pH of the composition is from 6 to 7.1 and the additional surfactant is sodium lauroyl glycinate.

7. The composition according to claim 1, wherein the composition further comprises cannabigerol and/or cannabidiol.

8. The composition according to claim 1, wherein the composition has from 40 to 82% by weight water, and a pH from 6.2 to 7.5.

9. The composition according to claim 1, wherein the first component comprises undecylenoyl phenylalanine and capryloyl glycine in a weight ratio from 2:1 to 1:2.

10. The composition according to claim 1, wherein the first component comprises undecylenoyl phenylalanine and the composition has a pH from 6.4 to 7.1 and water makes up from 40 to 82% by weight of the composition.

11. A method for treating skin by contacting the skin with the composition according to claim 1.

12. The composition according to claim 1 wherein the composition further comprises stearic acid, 12-hydroxystearic acid, palmitic acid, terpineol, thymol, lauric acid, retinoic acid precursor or a mixture thereof.

13. The composition according to claim 1 wherein the composition further comprises 4-ethyl resorcinol, 4-hexyl resorcinol, sunscreen, vitamin C, rosemary extract, sage, chamomile, sunscreen or a mixture thereof.

14. The composition according to claim 1 wherein sodium dehydroacetate makes up from 0.0 to less than 0.0125% by weight of the wash composition.

15. The composition according to claim 1 wherein the wash composition does not include a surfactant system with sulfates.

* * * * *